US011672556B2

(12) United States Patent
Baril et al.

(10) Patent No.: US 11,672,556 B2
(45) Date of Patent: Jun. 13, 2023

(54) VARIABLE ARTICULATION DRIVE FOR WRISTED ROBOTIC INSTRUMENTS

(71) Applicant: Covidien LP, Mansfield, MA (US)

(72) Inventors: Jacob C. Baril, Norwalk, CT (US); Nicolette R. LaPierre, Windsor Locks, CT (US); Matthew A. DiNino, Newington, CT (US)

(73) Assignee: COVIDIEN LP, Mansfield, MA (US)

(*) Notice: Subject to any disclaimer, the term of this patent is extended or adjusted under 35 U.S.C. 154(b) by 304 days.

(21) Appl. No.: 17/195,907

(22) Filed: Mar. 9, 2021

(65) Prior Publication Data

US 2021/0290321 A1 Sep. 23, 2021

Related U.S. Application Data

(60) Provisional application No. 62/992,205, filed on Mar. 20, 2020.

(51) Int. Cl.

*A61B 17/29* (2006.01)
*A61B 34/30* (2016.01)
*A61B 34/00* (2016.01)

(52) U.S. Cl.

CPC .............. *A61B 17/29* (2013.01); *A61B 34/30* (2016.02); *A61B 34/71* (2016.02); (Continued)

(58) Field of Classification Search

CPC .............. A61B 2034/305; A61B 17/29; A61B 2017/2908; A61B 2017/2902; A61B 34/71; A61B 2034/301; A61B 2017/320071; A61B 34/30; A61B 2017/003; A61B 2017/00314; A61B 2017/00318;

(Continued)

(56) References Cited

U.S. PATENT DOCUMENTS 5,792,165 A * 8/1998 Klieman ................ A61B 34/71 606/174
2011/0105843 A1 * 5/2011 Mueller ................ A61B 17/29 600/129

(Continued)

FOREIGN PATENT DOCUMENTS

WO 2016025132 A1 2/2016

*Primary Examiner* — Timothy J Neal
*Assistant Examiner* — James R McGinnity
(74) *Attorney, Agent, or Firm* — Carter, DeLuca & Farrell, LLP

(57) ABSTRACT

A surgical instrument includes an end effector having a first jaw member and a second jaw member movably coupled to one another; a wrist assembly having a distal end portion supporting the end effector; and a shaft defining a longitudinal axis and have a distal end supporting the wrist assembly. The wrist assembly includes a plurality of joint members rotatably connected to one another in tip-to-tail fashion, wherein each joint member defines a central rotational axis, and wherein adjacent joint members are rotatably connected to one another in a plane which is oriented at a non-orthogonal angle relative to the central rotational axes of the adjacent joint members. The wrist assembly includes also includes a plurality of concentric drive tubes extending through the plurality of joint members, wherein each drive tube includes a distal end keyed to a respective joint member.

20 Claims, 3 Drawing Sheets

(52) U.S. Cl.
CPC ................. *A61B 2017/2902* (2013.01); *A61B 2017/2908* (2013.01); *A61B 2034/305* (2016.02)

(58) Field of Classification Search
CPC .... A61B 2017/00323; A61M 25/0105; A61M 25/0133; A61M 25/0147
See application file for complete search history.

(56) References Cited

U.S. PATENT DOCUMENTS

| | | | | |
|---|---|---|---|---|
| 2012/0116416 | A1 | 5/2012 | Neff et al. | |
| 2012/0215220 | A1 * | 8/2012 | Manzo ................... | A61B 34/30 606/46 |
| 2014/0100558 | A1 * | 4/2014 | Schmitz ............... | A61B 17/285 606/174 |
| 2017/0258539 | A1 * | 9/2017 | Cohen .................... | A61B 17/28 |
| 2019/0298400 | A1 * | 10/2019 | Horeman ............... | A61B 17/29 |
| 2021/0220063 | A1 * | 7/2021 | Kapadia ..................... | B25J 9/12 |

* cited by examiner

VARIABLE ARTICULATION DRIVE FOR WRISTED ROBOTIC INSTRUMENTS

CROSS-REFERENCE TO RELATED APPLICATIONS

The present application claims the benefit of and priority to U.S. Provisional Patent Application Ser. No. 62/992,205, filed on Mar. 20, 2020, the entire content of which being hereby incorporated by reference.

BACKGROUND

Robotic surgical systems have been used in minimally invasive medical procedures. Some robotic surgical systems include a console supporting a robot arm, and at least one end effector such as forceps or a grasping tool that is mounted to the robot arm via a wrist assembly. During a medical procedure, the end effector and the wrist assembly are inserted into a small incision (via a cannula) or a natural orifice of a patient to position the end effector at a work site within the body of the patient.

In robotic surgical systems, cables extend from the robot console, through the robot arm, and connect to the wrist assembly and/or end effector. In some instances, the cables are actuated by means of motors that are controlled by a processing system including a user interface for a surgeon or clinician to be able to control the robotic surgical system including the robot arm, the wrist assembly and/or the end effector.

Existing wristed robotic instruments also have what is known as an elbowed design in which the end effector articulation point and the jaw pivot point are located at longitudinally spaced apart positions. Consequently, given the variety of positions in which these end effectors may be disposed to access surgical sites, one challenge associated with existing wristed robotic instruments is providing increased ranges of motions, access and reach to the wristed robotic instruments so as to enable a surgeon to perform greater numbers of surgical procedures.

Accordingly, a need exists for wristed robotic instruments that provide increased ranges of motions, access and reach which provide a surgeon with increased ability to perform greater numbers of surgical procedures.

SUMMARY

Accordingly, this disclosure details mechanical implementations for wristed robotic instruments that provide increased ranges of motions, access and reach to a surgeon, thereby enabling the surgeon to perform greater numbers of surgical procedures.

In accordance with one aspect, this disclosure is directed to a surgical instrument for a robotic surgical system. The surgical instrument includes an end effector having a first jaw member and a second jaw member movably coupled to one another; a wrist assembly having a distal end portion supporting the end effector; and a shaft defining a longitudinal axis and have a distal end supporting the wrist assembly. The wrist assembly includes a plurality of joint members rotatably connected to one another in tip-to-tail fashion, wherein each joint member defines a central rotational axis, and wherein adjacent joint members are rotatably connected to one another in a plane which is oriented at a non-orthogonal angle relative to the central rotational axes of the adjacent joint members. The wrist assembly includes also includes a plurality of concentric drive tubes extending through the plurality of joint members, wherein each drive tube includes a distal end keyed to a respective joint member.

The plurality of joint members may be rotatable relative to one another. The plurality of joint members may be rotatable relative to the shaft.

It is contemplated that a number of joint members may equal a number of drive tubes.

At least a distal end portion of each drive tube may have a non-circular transverse cross-sectional profile.

Each joint member may define a distal end surface and a proximal end surface. Each of the distal end surface and the proximal end surface may define a plane that is oriented at an angle relative to the central longitudinal rotation axis of the respective joint member.

The plurality of joint members of the wrist assembly may have a stove-pipe construction.

At least one drive cable may extend through a lumen of an inner-most drive tube of the plurality of concentric drive tubes.

A distal end of the at least one drive cable may be operatively connected to the end effector to effectuate actuation of the end effector.

An inner-most drive tube of the plurality of concentric drive tubes may be keyed to a distal-most joint member of the plurality of joint members.

A drive tube radially adjacent to the inner most drive tube of the plurality of concentric drive tubes may be keyed to a joint member proximally adjacent to the distal-most joint member of the plurality of joint members.

According to another aspect of the disclosure, a surgical instrument for a robotic surgical system is provided. The surgical instrument includes an end effector having a first jaw member and a second jaw member movably coupled to one another; a wrist assembly having a distal end portion supporting the end effector; and a shaft defining a longitudinal axis and have a distal end supporting the wrist assembly. The wrist assembly includes at least a first joint member and a second joint member rotatably connected to one another in tip-to-tail fashion, wherein each joint member defines a central rotational axis, and wherein the first joint member and the second joint member are rotatably connected to one another in a plane which is oriented at a non-orthogonal angle relative to the central rotational axes of the first joint member or second joint member, wherein the second joint member is disposed proximal of the first joint member. The wrist assembly further includes at least a first drive tube and a second drive tube concentrically and rotatably disposed externally of the first drive tube, the first drive tube and the second drive tube extending through the first joint member and the second joint member, wherein the first drive tube includes a distal end keyed to the first joint member and wherein the second drive tube includes a distal end keyed to the second joint member.

The first joint member and the second joint member may be independently rotatable relative to the shaft.

At least a distal end portion of each drive tube may have a non-circular transverse cross-sectional profile.

Each joint member may define a distal end surface and a proximal end surface. Each of the distal end surface and the proximal end surface may define a plane that is oriented at an angle relative to the central longitudinal rotation axis of the respective joint member.

The joint members of the wrist assembly may define a stove-pipe construction.

The surgical instrument may further include at least one drive cable extending through a lumen of the first drive tube.

A distal end of the at least one drive cable may be operatively connected to the end effector to effectuate actuation of the end effector.

The first joint member and the second joint member may be part of a plurality of joint members rotatably connected to one another in tip-to-tail fashion. Each joint member may define a central rotational axis, and wherein adjacent joint members may be rotatably connected to one another in a plane which is oriented at a non-orthogonal angle relative to the central rotational axes of the adjacent joint members.

The first drive tube and the second drive tube may be part of a plurality of concentric drive tubes extending through the plurality of joint members. Each drive tube may include a distal end keyed to a respective joint member.

Other aspects, features, and advantages will be apparent from the description, the drawings, and the claims that follow.

BRIEF DESCRIPTION OF DRAWINGS

The accompanying drawings, which are incorporated in and constitute a part of this specification, illustrate embodiments of the disclosure and, together with a general description of the disclosure given above and the detailed description given below, serve to explain the principles of the disclosure, wherein:

FIG. 2B1 is a schematic transverse cross-sectional view of the wrist assembly of the surgical instrument of the robotic surgical system illustrated in FIG. 2B, as taken through 2B1-2B1 of FIG. 2B;

FIG. 2B2 is a schematic transverse cross-sectional view of the wrist assembly of the surgical instrument of the robotic surgical system illustrated in FIG. 2B, as taken through 2B2-2B2 of FIG. 2B;

FIG. 2B3 is a schematic transverse cross-sectional view of the wrist assembly of the surgical instrument of the robotic surgical system illustrated in FIG. 2B, as taken through 2B3-2B3 of FIG. 2B;

FIG. 2B4 is a schematic transverse cross-sectional view of the wrist assembly of the surgical instrument of the robotic surgical system illustrated in FIG. 2B, as taken through 2B4-2B4 of FIG. 2B;

FIG. 2B5 is a schematic transverse cross-sectional view of the wrist assembly of the surgical instrument of the robotic surgical system illustrated in FIG. 2B, as taken through 2B5-2B5 of FIG. 2B;

FIG. 3 is a distal end view of the wrist assembly illustrated in FIG. 2C; and FIG. 4 is a schematic illustration of the wrist assembly of FIG. 2A shown in an articulated condition.

DETAILED DESCRIPTION

Figure 1:
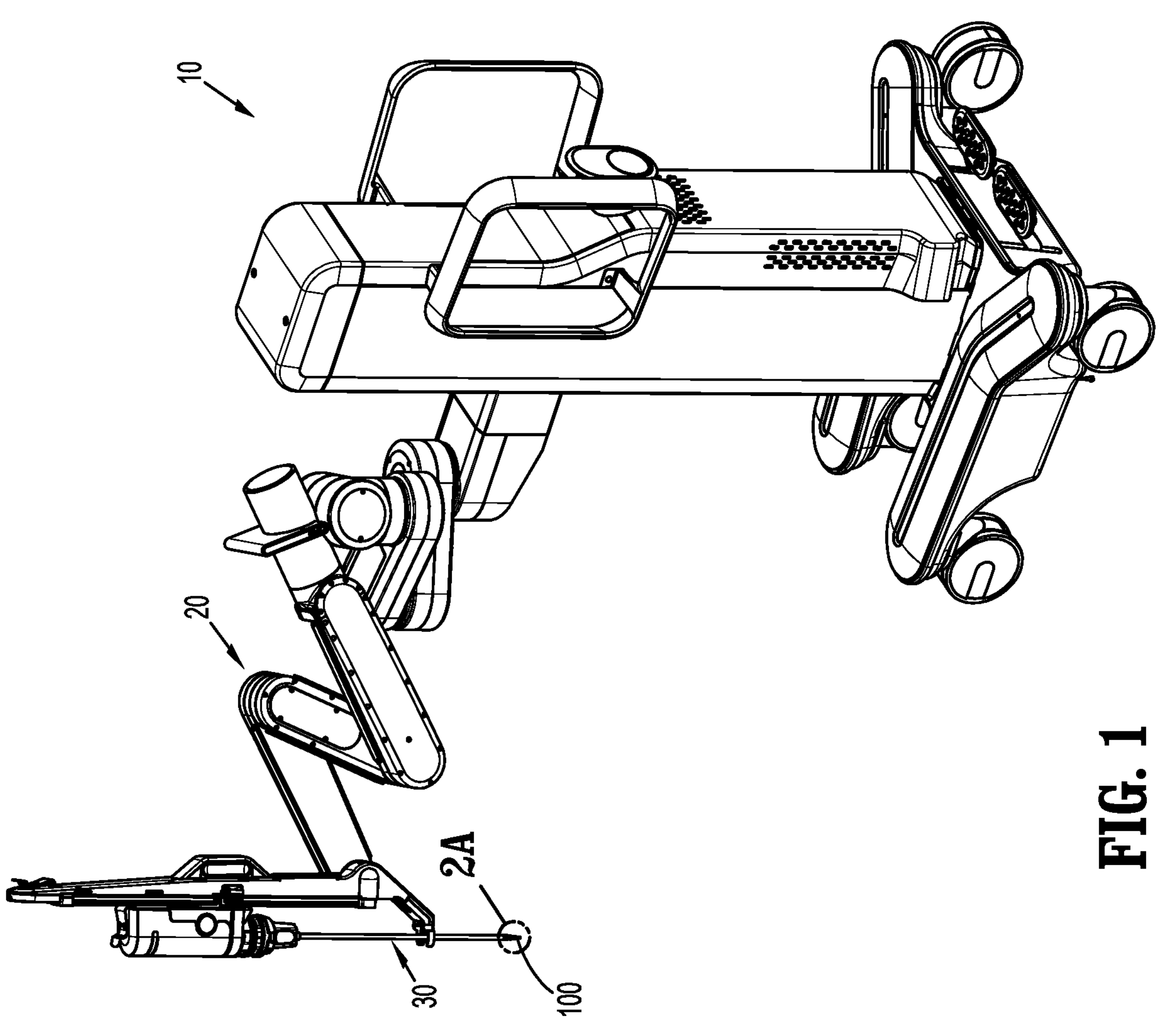
FIG. 1 is a perspective view of a robotic surgical system in accordance with this disclosure.

Embodiments of the present disclosure are described in detail with reference to the drawings, in which like reference numerals designate identical or corresponding elements in each of the several views. As commonly known, the term "clinician" refers to a doctor, surgeon, a nurse, or any other care provider and may include support personnel. Additionally, the term "proximal" refers to the portion of structure that is closer to the clinician or further from the patient or target, and the term "distal" refers to the portion of structure that is farther from the clinician or closer to the patient or target. In addition, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

With brief reference to FIG. 1, a robotic surgical system 10 is shown and includes a robotic arm 20 that supports a wristed surgical instrument 30 having an end effector 100. Robotic surgical system 10 employs various robotic elements to assist the clinician and allow remote operation (or partial remote operation) of surgical instrumentation such as surgical instrument 30. Various robotic arms, gears, cams, pulleys, electric and mechanical motors, etc. may be employed for this purpose and may be designed with robotic surgical system 10 to assist the clinician during the course of an operation or treatment.

Robotic surgical system 10 may be employed with one or more consoles (not shown) that are next to the operating theater or located in a remote location. In this instance, one team of clinicians may prep the patient for surgery and configure the robotic surgical system with one or more of the instruments/end effectors disclosed herein while another clinician (or group of clinicians) remotely controls the instruments/end effectors via robotic surgical system 10. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416 and PCT Application Publication No. WO2016/025132, the entire contents of each of which are incorporated by reference herein.

Turning now to FIGS. 2A-2C and FIGS. 3-4, surgical instrument 30 includes an elongate shaft 32 supporting the end effector 100 on a distal end thereof. Shaft 32 defines a longitudinal axis "X-X" about which end effector 100 can rotate. End effector 100 includes a jaw assembly 110 having a top or first jaw member 112, and a bottom or second jaw member 114 coupled to first jaw member 112. Jaw assembly 110 is connected to the distal end of shaft 32 by a wrist assembly 120. Jaw assembly 110 is positioned at a distal end of the wrist assembly 120 so as to be articulated relative to axis "X-X" upon actuation of wrist assembly 120, as described below. Jaw assembly 110 of end effector 100 is coupled to one or more cables "C" (see FIG. 2C), push/pull rods (not shown), or the like, of surgical instrument 30 that are robotically actuatable to impart such actuation and/or pivoting movement to jaw assembly 110.

Wrist assembly 120 includes several joint members 130 rotatably interconnected with one another in tip-to-tail fashion. Specifically, each joint member 130 is tubular or cylindrical and defines a central longitudinal rotation axis. Each joint member 130 may have at least one end surface (e.g., distal end surface or proximal end surface) thereof that defines a plane and which plane is chamfered at an angle relative to the central longitudinal rotation axis thereof, in the form of a stove pipe. By way of example only, wrist assembly 120 includes a proximal-most joint member 32*a* formed or provided at a distal end of shaft 32, a first joint member 130*a* rotatably connected to a distal end of proximal-most joint member 32*a*, a second joint member 130*b* rotatably connected to a distal end of first joint member 130*a*, a third joint member 130*c* rotatably connected to a distal end of second joint member 130*b*, and a fourth or distal-most joint member 130*d* rotatably connected to a distal end of third joint member 130*c* and supporting jaw assembly 110.

It is contemplated that each joint member 130 is journaled with one another whereby, in combination with the chamfered interfacing ends thereof, as one joint member 130 is rotated, about its central rotational axis, relative to an adjacent joint member 130, the respective central rotational axes thereof are caused to be moved between an in-line condition and an angled condition relative to one another. It is contemplated that the chamfered end surfaces may be angled between 0° to 45° relative to the central rotational axis of a respective joint member 130. It is further contemplated that the chamfered end surfaces may be oriented at an angle that is not orthogonal to the central rotational axis of a respective joint member 130.

Surgical instrument 30 includes a wrist actuation assembly 140 rotatably extending through shaft 32, and operatively engaged with wrist assembly 120. Specifically, wrist actuation assembly 140 includes a plurality of concentrically arranged drive tubes 142 which are rotatable relative to one another, and which are concentric with the longitudinal axis "X-X" of shaft 32. Each drive tube 142 includes a proximal end portion (not shown) in operative engagement with a driving member (e.g., a motor), and a distal end portion 144 in operative engagement with a respective joint member 130.

Specifically, wrist actuation assembly 140 includes a first drive tube 142*a* having at least a non-circular distal end portion 144*a* keyed to first joint member 130*a*, a second drive tube 142*b* having at least a non-circular distal end portion 144*b* keyed to second joint member 130*b*, a third drive tube 142*c* having at least a non-circular distal end portion 144*c* keyed to third joint member 130*c*, and a fourth drive tube 142*d* having at least a non-circular distal end portion 144*d* keyed to fourth or distal-most joint member 130*d*.

It is contemplated that surgical instrument 30 includes a drive tube 142*a*-142*d* for a respective joint member 130*a*-130*d*, e.g., one for one, two for two, three for three, four for four, etc. Additionally, a central or inner-most drive member (e.g., drive member 142*d*) is keyed to a distal-most joint member (e.g., joint member 130*d*), and an outer-most drive member (e.g., 142*a*) is keyed to a proximal-most joint member of the rotatably joint members (e.g., joint member 130*a*). Further, the next drive member radially inward of drive member 142*a* (e.g., drive member 142*b*) is keyed to a joint member located distally adjacent to joint member 130*a* (e.g., joint member 130*b*). Still further, the next drive member radially inward of drive member 142*b* and outward of drive member 142*d* (e.g., drive member 142*c*) is keyed to a joint member located distally adjacent to joint member 130*b* and proximal of joint member 130*d* (e.g., joint member 130*c*).

Figure 2C:
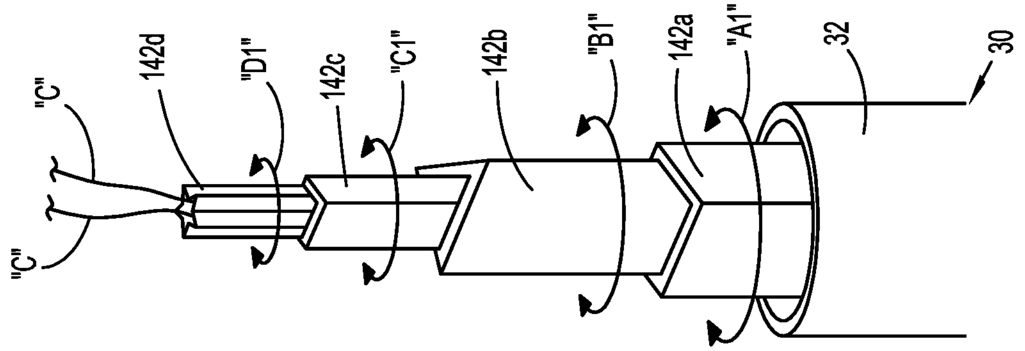
FIG. 2C is a schematic perspective view of an inner portion of the wrist assembly of FIGS. 2A and 2B.
Figure 2B:
FIG. 2B illustrates several schematic transverse cross-sectional views of the wrist assembly of a surgical instrument of the robotic surgical system of this disclosure, as taken through various joint members of the wrist assembly.
Figure 2B:
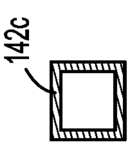
Figure 2B:
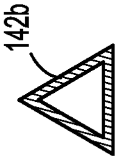
Figure 2B:
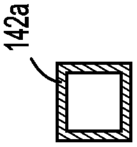
Figure 2B:
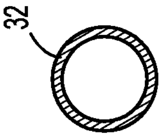
Figure 2A:
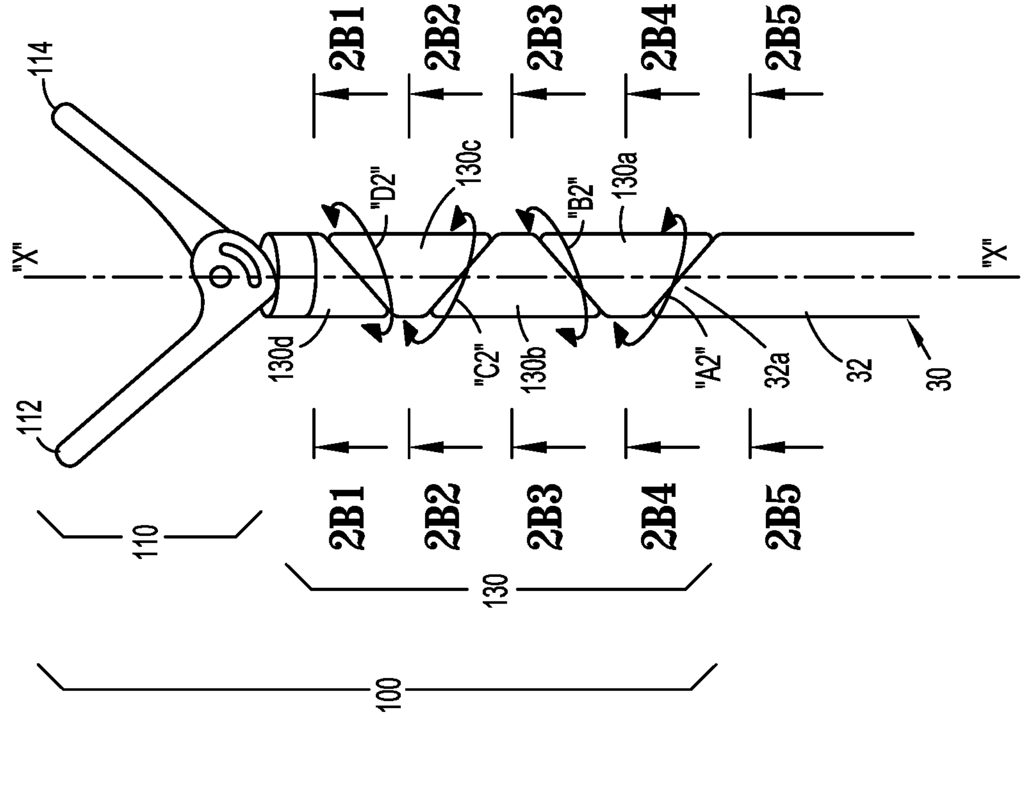
FIG. 2A is an enlarged schematic view of the indicated area of detail of FIG. 1.
Figure 3:
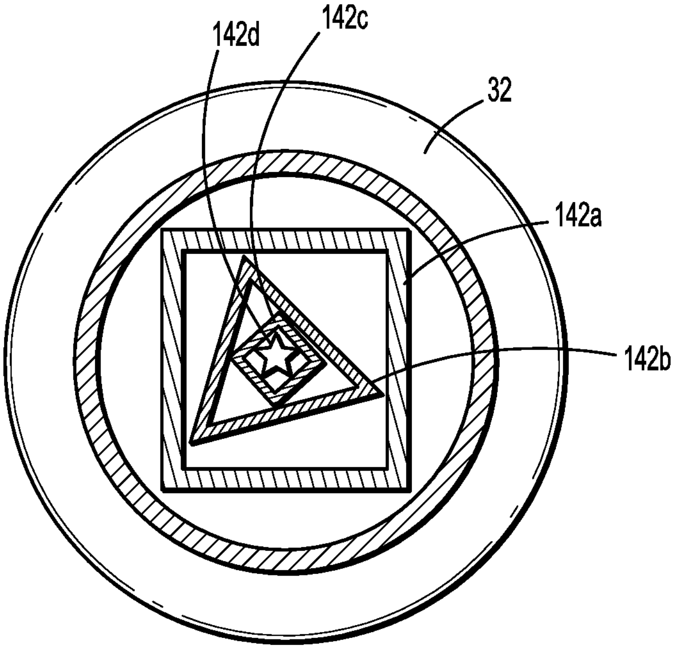

With reference to FIGS. 2B and 2C, while at least the distal end portions 144*a*-144*d* or respective drive tubes 142*a*-142*d* are illustrated as having a rectangular, a triangular, a rectangular, and a starred transverse cross-sectional profile, it is contemplated that each distal end portion 144*a*-144*d* may have the same transverse non-circular cross-sectional profile as one another or a different transverse non-circular cross-sectional profile from one another. It is further contemplated that each distal end portion 144*a*-144*d* may have a toothed or geared profile, and more specifically a helical or worm gear outer profile for engaging a complementary mating structure formed in or on a respective joint member 130*a*-103*d*.

In use, as first drive tube 142*a* is caused to be rotated (as indicated by arrow "A1" of FIG. 2C) by a driving member, e.g., a motor (not shown), distal end portion 144*a* of first drive tube 142*a* acts on first joint member 130*a* of wrist assembly 130 to cause first joint member 130*a* to rotate (as indicated by arrow "A2" of FIG. 2A) about its central rotational axis relative to the proximal-most joint member 32*a* of shaft 32. Due to first joint member 130*a* and proximal-most joint member 32*a* being rotatably coupled to one another along a chamfer, as first joint member 130*a* is rotated relative to proximal-most joint member 32*a*, the central axis of rotation of first joint member 130*a* is caused to be changed relative to the longitudinal axis "X-X" of shaft 32. In so doing, all components of surgical instrument 30, distal of proximal-most joint member 32*a*, are caused to be moved or angled relative to the longitudinal axis "X-X" of shaft 32.

Further in use, as second drive tube 142*b* is caused to be rotated (as indicated by arrow "B1" of FIG. 2C) by a driving member, e.g., a motor (not shown), distal end portion 144*b* of second drive tube 142*b* acts on second joint member 130*b* of wrist assembly 130 to cause second joint member 130*b* to rotate (as indicated by arrow "B2" of FIG. 2A) about its central rotational axis relative to the first joint member 130*a*. Due to second joint member 130*b* and first joint member 130*a* being rotatably coupled to one another along a chamfer, as second joint member 130*b* is rotated relative to first joint member 130*a*, the central axis of rotation of second joint member 130*b* is caused to be changed relative to the central longitudinal axis of first joint member 130*a*. In so doing, all components of surgical instrument 30, distal of first joint member 130*a*, are caused to be moved or angled relative to the longitudinal axis "X-X" of shaft 32.

Still further in use, as third drive tube 142*c* is caused to be rotated (as indicated by arrow "C1" of FIG. 2C) by a driving member, e.g., a motor (not shown), distal end portion 144*c* of third drive tube 142*c* acts on third joint member 130*c* of wrist assembly 130 to cause third joint member 130*c* to rotate (as indicated by arrow "C2" of FIG. 2A) about its central rotational axis relative to the second joint member 130*b*. Due to third joint member 130*c* and second joint member 130*b* being rotatably coupled to one another along a chamfer, as third joint member 130*c* is rotated relative to second joint member 130*b*, the central axis of rotation of third joint member 130*c* is caused to be changed relative to the central longitudinal axis of second joint member 130*b*. In so doing, all components of surgical instrument 30, distal of second joint member 130*b*, are caused to be moved or angled relative to the longitudinal axis "X-X" of shaft 32.

Additionally in use, as fourth drive tube 142*d* is caused to be rotated (as indicated by arrow "D1" of FIG. 2C) by a driving member, e.g., a motor (not shown), distal end portion 144*d* of fourth drive tube 142*d* acts on fourth joint member 130*d* of wrist assembly 130 to cause fourth joint member 130*d* to rotate (as indicated by arrow "D2" of FIG. 2A) about its central rotational axis relative to the third joint member 130*c*. Due to fourth joint member 130*d* and third joint member 130*c* being rotatably coupled to one another along a chamfer, as fourth joint member 130*d* is rotated relative to third joint member 130*c*, the central axis of rotation of fourth joint member 130*d* is caused to be changed relative to the central longitudinal axis of third joint member 130*c*. In so doing, all components of surgical instrument 30, distal of third joint member 130*c*, are caused to be moved or angled relative to the longitudinal axis "X-X" of shaft 32.

Figure 4:
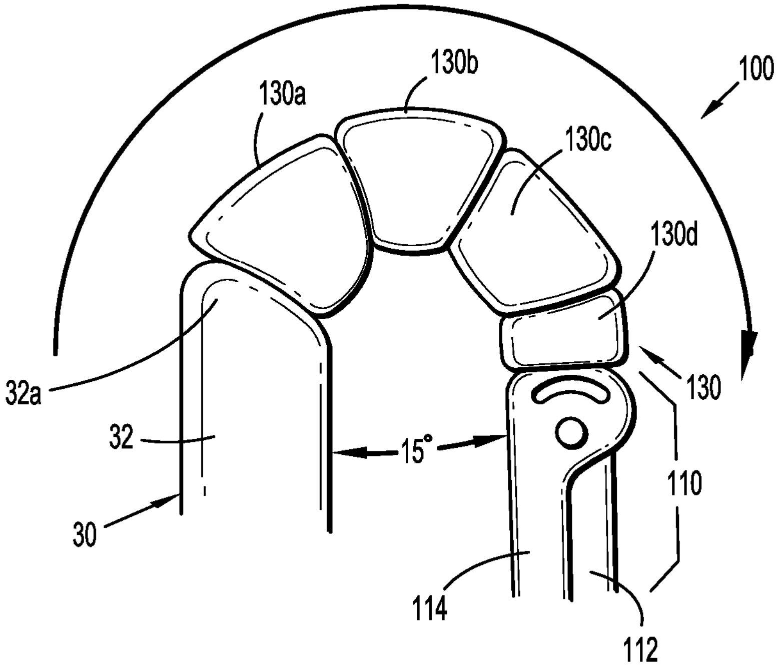

In accordance with the disclosure, it is contemplated that rotation of drive tubes 142*a*-142*d*, via respective motors or the like (not shown), is coordinated in such a manner by robotic surgical system 10, that various orientations and configurations for wrist assembly 130 may be achieved. For example, drive tubes 142*a*-142*d* may be respectively rotated such that wrist assembly 130 may be angled only at one joint member 32*a*, 130*a*-130*d*, at multiple joint members 32*a*, 130*a*-130*d*, or at all joint members 32*a*, 130*a*-130*d* (as illustrated in FIG. 4) to achieve an angle of inclination of about 15° between the longitudinal X-X axis of shaft 32 and a longitudinal axis of the end effector 100. It is further contemplated that drive tubes 142*a*-142*d* may be respectively rotated such that wrist assembly 130 may achieve a goose-neck configuration.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

The invention claimed is:

1. A surgical instrument for a robotic surgical system, the surgical instrument comprising: an end effector having a first jaw member and a second jaw member movably coupled to one another; a wrist assembly having a distal end portion supporting the end effector, the wrist assembly including: a plurality of joint members rotatably connected to one another in tip-to-tail fashion, wherein each joint member defines a central rotational axis, and wherein adjacent joint members are rotatably connected to one another in a plane which is oriented at a non-orthogonal angle relative to the central rotational axes of the adjacent joint members; and a plurality of concentric drive tubes extending through the plurality of joint members, wherein each drive tube includes a distal end keyed to a respective joint member; and a shaft defining a longitudinal axis, the shaft having a distal end supporting the wrist assembly.

2. The surgical instrument according to claim 1, wherein the plurality of joint members are rotatable relative to one another.

3. The surgical instrument according to claim 1, wherein the plurality of joint members are rotatable relative to the shaft.

4. The surgical instrument according to claim 1, wherein a number of joint members of the plurality of joint members equals a number of drive tubes of the plurality of drive tubes.

5. The surgical instrument according to claim 1, wherein at least a distal end portion of each drive tube of the plurality of drive tubes has a non-circular transverse cross-sectional profile.

6. The surgical instrument according to claim 1, wherein each joint member of the plurality of joint members defines a distal end surface and a proximal end surface, and wherein each of the distal end surface and the proximal end surface defines a plane that is oriented at an angle relative to the central longitudinal rotation axis of the respective joint member from the plurality of joint members.

7. The surgical instrument according to claim 1, wherein the plurality of joint members of the wrist assembly have a stove-pipe construction.

8. The surgical instrument according to claim 1, further comprising at least one drive cable extending through a lumen of an inner-most drive tube of the plurality of concentric drive tubes.

9. The surgical instrument according to claim 8, wherein a distal end of the at least one drive cable is operatively connected to the end effector to effectuate actuation of the end effector.

10. The surgical instrument according to claim 1, wherein an inner-most drive tube of the plurality of concentric drive tubes is keyed to a distal-most joint member of the plurality of joint members.

11. The surgical instrument according to claim 10, wherein a drive tube radially adjacent to the inner most drive tube of the plurality of concentric drive tubes is keyed to a joint member proximally adjacent to the distal-most joint member of the plurality of joint members.

12. A surgical instrument for a robotic surgical system, the surgical instrument comprising: an end effector having a first jaw member and a second jaw member movably coupled to one another; a wrist assembly having a distal end portion supporting the end effector, the wrist assembly including: at least a first joint member and a second joint member rotatably connected to one another in tip-to-tail fashion, wherein each joint member defines a central rotational axis, and wherein the first joint member and the second joint member are rotatably connected to one another in a plane which is oriented at a non-orthogonal angle relative to the central rotational axes of the first joint member or second joint member, wherein the second joint member is disposed proximal of the first joint member; and at least a first drive tube and a second drive tube concentrically and rotatably disposed externally of the first drive tube, the first drive tube and the second drive tube extending through the first joint member and the second joint member, wherein the first drive tube includes a distal end keyed to the first joint member and wherein the second drive tube includes a distal end keyed to the second joint member; and a shaft defining a longitudinal axis, the shaft having a distal end supporting the wrist assembly.

13. The surgical instrument according to claim 12, wherein the first joint member and the second joint member are independently rotatable relative to the shaft.

14. The surgical instrument according to claim 12, wherein at least a distal end portion of each drive tube has a non-circular transverse cross-sectional profile.

15. The surgical instrument according to claim 12, wherein each joint member defines a distal end surface and a proximal end surface, and wherein each of the distal end surface and the proximal end surface defines a plane that is oriented at an angle relative to the central longitudinal rotation axis of the respective joint member.

16. The surgical instrument according to claim 12, wherein the joint members of the wrist assembly define a stove-pipe construction.

17. The surgical instrument according to claim 12, further comprising at least one drive cable extending through a lumen of the first drive tube.

18. The surgical instrument according to claim 17, wherein a distal end of the at least one drive cable is operatively connected to the end effector to effectuate actuation of the end effector.

19. The surgical instrument according to claim 12, wherein the first joint member and the second joint member are part of a plurality of joint members, wherein each joint member of the plurality of joint members is rotatably connected to one another in tip-to-tail fashion, wherein each joint member of the plurality of joint members defines a central rotational axis, and wherein adjacent joint members of the plurality of joint members are rotatably connected to one another in a plane which is oriented at a non-orthogonal angle relative to the central rotational axes of the adjacent joint members of the plurality of joint members.

20. The surgical instrument according to claim 19, wherein the first drive tube and the second drive tube are part of a plurality of concentric drive tubes extending through the plurality of joint members, wherein each drive tube of the plurality of drive tubes includes a distal end keyed to a respective joint member of the plurality of joint members.

* * * * *